United States Patent
Masilamani et al.

(10) Patent No.: US 9,726,679 B2
(45) Date of Patent: Aug. 8, 2017

(54) SPECTRAL METHOD FOR QUANTIFYING HEMOGLOBIN FRAGILITY CAUSED BY SMOKING

(71) Applicant: KING SAUD UNIVERSITY, Riyadh (SA)

(72) Inventors: Vadivel Masilamani, Riyadh (SA); Mohamad Saleh Alsalhi, Riyadh (SA); Sandhanasamy Devanesan, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 14/811,793

(22) Filed: Jul. 28, 2015

(65) Prior Publication Data

US 2017/0030931 A1    Feb. 2, 2017

(51) Int. Cl.
*G01N 31/22* (2006.01)
*G01N 33/50* (2006.01)
*G01N 33/72* (2006.01)

(52) U.S. Cl.
CPC .................. *G01N 33/721* (2013.01)

(58) Field of Classification Search
CPC ...... G01N 33/721; G01N 33/72; G01N 33/50; G01N 33/00; G01N 33/48; G01N 21/64; G01N 21/63
USPC .......................................................... 436/66
See application file for complete search history.

(56) References Cited

U.S. PATENT DOCUMENTS

| | | | |
|---|---|---|---|
| 4,378,971 A | 4/1983 | Schwartz | |
| 7,109,038 B2 | 9/2006 | Scholl et al. | |
| 7,113,814 B2 | 9/2006 | Ward et al. | |
| 7,869,033 B2 | 1/2011 | Masilamani et al. | |
| 8,208,142 B2 | 6/2012 | Masilamani et al. | |
| 2004/0064053 A1 | 4/2004 | Chang et al. | |
| 2010/0075367 A1 | 3/2010 | Masilamani et al. | |
| 2012/0052516 A1* | 3/2012 | Baudin-Creuza .... | G01N 33/721 435/7.92 |

OTHER PUBLICATIONS

Al-Thunayan, Montaha Ahmad, Cancer Diagnosis by Synchronous Fluorescence Spectra of Blood and Urine Components, Kingdom of Saudi Arabia, King Saud University, 2006, pp. 1-127.*
Madhikarmi, Laxmi, Role of Cigarette Smoking on Lipid Peroxidation and Antioxidant Parameters in Iron Deficiency Anemic Individuals, The Experiment, Feb. 2013, vol. 7, No. 3, pp. 404-412.*
Roy et al, Cigarette smokers develop structurally modified hemoglobin: a possible way of increasing oxidative stress, Inhalation Toxicology, May 2015, 27:6, 300-307.*
Ebenezar J. et al, Optical Biopsy of Cancer Using Native Fluorescence Spectroscopy, National Laser Symposium Proceedings, Dec. 22-24, 2003, pp. 96-99.*
Weston et al., "Fluorescence and mass spectral evidence of the formation of benzo[a]pyrene anti-diol-epoxide-DNA and -hemoglobin adducts in humans", Carcinogenesis, Jan. 1, 1989, 10, 251-257.

* cited by examiner

*Primary Examiner* — Christine T Mui
(74) *Attorney, Agent, or Firm* — Richard C. Litman

(57) ABSTRACT

The spectral method for quantifying hemoglobin fragility caused by smoking is based on decreased concentration of tryptophan and elevated concentrations of the biomolecules nicotinamide adenine dinucleotide (NADH), flavin adenine dinucleotide (FAD), and porphyrin in the presence of hemoglobin fragility. The method involves the steps of obtaining a blood sample from a patient who is a smoker; separating blood plasma from the samples; obtaining synchronous excitation spectra (SXS) of the blood plasma with a spectrofluorometer at a scan offset of 70 nm and at a scan offset of 10 nm; comparing the patient's SXS with the SXS of normal control samples; and diagnosing hemoglobin fragility when the excitation maxima of NADH, FAD, and porphyrin are between 30% and 70% higher than the maxima for these metabolites in the normal control samples, or when the excitation maximum for tryptophan is 60% of the control sample.

1 Claim, 2 Drawing Sheets ns of blood, # SPECTRAL METHOD FOR QUANTIFYING HEMOGLOBIN FRAGILITY CAUSED BY SMOKING

BACKGROUND OF THE INVENTION

1. Field of the Invention

The present invention relates to disorders of the blood, and particularly to a spectral method for quantifying hemoglobin fragility caused by smoking that uses fluorescence spectroscopy techniques, particularly synchronous scanning spectroscopy, to measure metabolites in blood plasma.

2. Description of the Related Art

According to a webmed report and the National Institutes of Health of the United States, 90% of death by lung cancer, 80% by chronic obstructive pulmonary diseases (COPD) and 17% due to heart diseases are caused by smoking tobacco in some form or the other. This is because tobacco smoke contains nicotine and 4,000 chemicals, including CO, benzene and oxidant gases. The adverse effects on health due to smoking depend upon a quantity called a pack year, which is a product of a cigarette packet and number of years of smoking.

A person who smokes one cigarette packet (of 20 in number) every day for one year is called one pack year. It is important to mention that smoking one pack per day over 10 years is more harmful than two packs for 5 years, although it means 10 pack years in both cases.

An important smoking-induced health hazard is an excessive circulation of carbon monoxide (CO) in the blood. Hemoglobin (FM) has 200 times greater affinity for CO than for oxygen ($O_2$) so that CO easily binds to Hb, producing cherry red blood (due to abnormal elevation of carboxy hemoglobin). This kind of "corruption" in blood leads to deprivation of $O_2$ in the blood stream, eventually leading to reduced lifespan of Hb. This may be the cause of smoking-induced Hb fragility. In spite of the above well known facts, there is no technique or instrument to quantify the smoking induced hemoglobin (Hb) fragility. There is a need to diagnose and quantify the degree of hemoglobin fragility resulting from smoking.

Thus, a spectral method for quantifying hemoglobin fragility caused by smoking solving the aforementioned problems is desired.

SUMMARY OF THE INVENTION

The spectral method for quantifying hemoglobin fragility caused by smoking is based on decreased concentration of tryptophan and elevated concentrations of the biomolecules nicotinamide adenine dinucleotide (NADH), flavin adenine dinucleotide (FAD), and porphyrin in the presence of hemoglobin fragility. The method involves the steps of obtaining a blood sample from a patient who is a smoker; separating blood plasma from the samples; obtaining synchronous excitation spectra (SXS) of the blood plasma with a spectrofluorometer at a scan offset of 70 nm and at a scan offset of 10 nm; comparing the patient's SXS with the SXS of normal control samples; and diagnosing hemoglobin fragility when the excitation maxima of NADH, FAD, and porphyrin are between 30% and 70% higher than the maxima for these metabolites in the normal control samples, or when the excitation maximum for tryptophan is 60% of the control sample.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
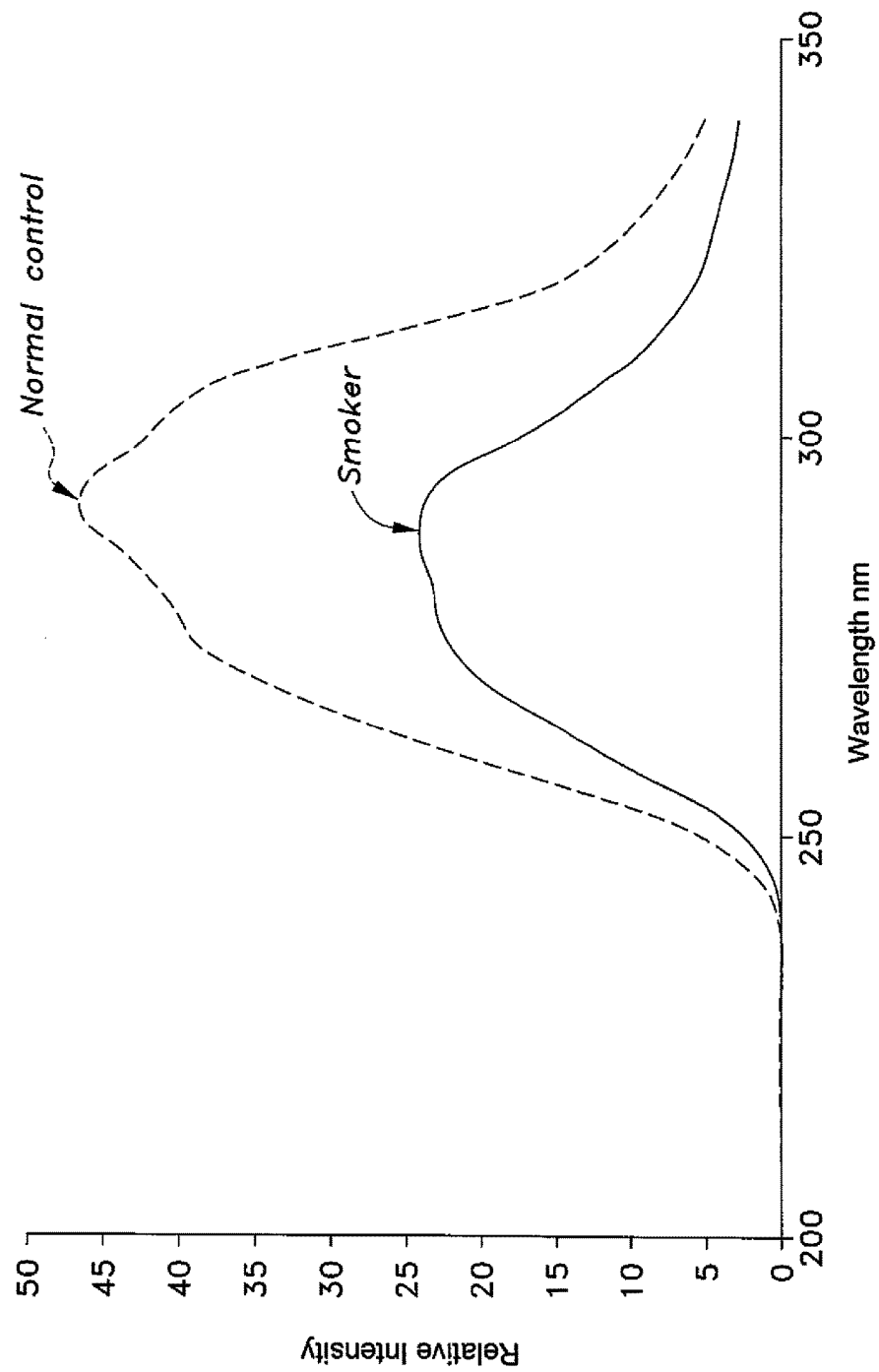
FIG. 1 is an exemplary Synchronous Excitation Spectra (SXS) of blood plasma of a normal control and a smoker at $\Delta\lambda = 70$ nm.

The spectral method for quantifying hemoglobin fragility caused by smoking is based on decreased concentration of tryptophan and elevated concentrations of the biomolecules nicotinamide adenine dinucleotide (NADH), flavin adenine dinucleotide (FAD), and porphyrin in the presence of hemoglobin fragility. The method involves the steps of obtaining a blood sample from a patient who is a smoker; separating blood plasma from the samples; obtaining synchronous excitation spectra (SXS) of the blood plasma with a spectrofluorometer at a scan offset of 70 nm and at a scan offset of 10 nm; comparing the patient's SXS with the SXS of normal control samples; and diagnosing hemoglobin fragility when the excitation maxima of NADH, FAD, and porphyrin are between 30% and 70% higher than the maxima for these metabolites in the normal control samples, or when the excitation maximum for tryptophan is 60% of the control sample. The method is based on the difference in the concentration of fluorescent biomolecules, which indirectly act as biomarkers for each type of disease.

EXAMPLE

For controls, exactly 5 ml of venous blood from each of the 43 healthy volunteers (age range: 20-50 years) was collected in a violet sterile vial that contained the anticoagulant EDTA. The vial was gently rocked five times to adequately mix the EDTA and whole blood, and the samples were centrifuged at 4,000 rotational speed (rpm) for 15 minutes. Clear, pale, greenish-yellow plasma supernatant was obtained by such centrifugation. A total of 1.5 ml of supernatant was removed from the top layer for spectrofluorimetric analysis, leaving the buffy coat (the white blood cells) and the formed elements (the red blood cells) as undisturbed sediment. The blood plasma sample was subjected to synchronous fluorescence excitation spectral analyses without any other treatment.

For smokers, the same protocol was used to process blood samples from confirmed smokers (age range: 20-50 years). Samples were collected from King Khalid Medical Hospital, Riyadh, KSA. The patients were informed about the investigation, and proper consent was obtained.

The instrument used was a spectrofluorometer (Perkin Elmer LS 55 USA) capable of collecting excitation, emission, and synchronous spectra in the 200-800 nm range. An excitation and emission slit width of 10 nm and scan speeds of 1000 nm/min were used. The samples were placed in quartz cuvettes and illuminated by a specified wavelength of light with a 10 nm spectral width and s spot size of 3×2 mm. The power at the point of illumination was approximately 20

µW, which was too low to induce photo bleaching. This finding was confirmed by repeating the experiment three times for each sample and observing no inter-replicate spectral differences.

The types of spectra are measured in the field of fluorescence spectroscopy. In synchronous excitation spectra (SXS), both gratings are synchronously rotated at offsets of 40 nm or 70 nm to obtain the fluorescence excitation bands for every molecule in the predetermined range. The wavelength offset and scan range are not unique. They are determined empirically by trial and error for a given set of experimental protocol. After analyzing other offsets, including 20 nm and 30 nm, it was found out that the 70 nm and 10 nm offset provided excellent resolution and good contrast between the normal and smoker samples because 70 nm offset leads to well resolved excitation spectra of three major biofluorophores (e.g. tryptophan, nicotinamide adenine dinucleotide etc.) in blood plasma. Hence, all of the results presented for plasma were based on the synchronous spectra. Similarly synchronous scan of 10 nm offset leads to well resolved emission spectra.

There are two figures that provide an exemplary measure of the damage done to Hb. In FIG. 1, we preset the SXS ($\Delta\lambda=70$ nm) of blood plasma of a normal control patient and a patient who is a smoker. There is a band (due to the amino acid tryptophan) at 290 nm. This is 50 units for normal, but only 30 units for a smoker of 10 pack years. That is the amino acid tryptophan, which is produced only at 60% of optimum level in the smoker.

Figure 2:
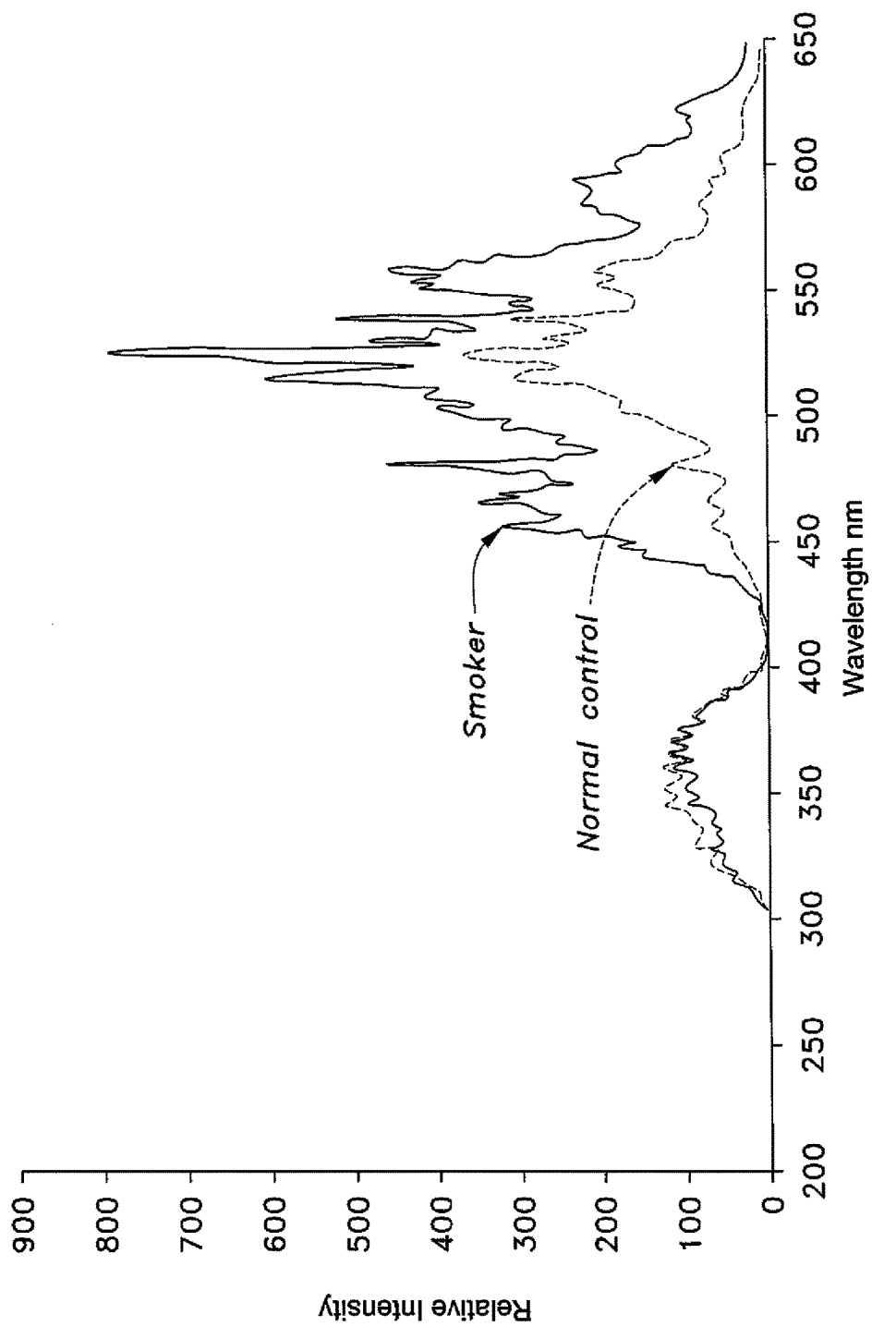
FIG. 2 is an exemplary Synchronous Excitation Spectra (SXS) of blood plasma of a normal control and a smoker at $\Delta\lambda = 10$ nm according to the present invention.

In FIG. 2, we represent the SXS ($\Delta\lambda=10$ nm) of blood plasma of a normal control patient and a patient who is a smoker. There are three main bands, one at 360 nm, 450 nm and 525 nm for both samples. It can be seen that the spectra for the smoker is out of proportion in comparison to the normal control. In order to distinguish the damage caused by smoking, we define three ratio parameters based on the intensities of these bands: $R_1=I_{550}/I_{360}$ (FAD concentration/tryptophan), $R_2=I_{360}/I_{555}$, and $R_3=I_{585}/I_{360}$. One can see that $R_1=1$, $R_2=0.5$, $R_3=0.84$ for the normal control; but 0.5, 0.3, and 1.5 for the smoker, or in other words, the spectral features go awry for smokers.

This is because for a smoker's plasma, the bands corresponding to NADH (nicotinamide adenine dinucleotide) [450 nm]; FAD (Flavin adenine dinucleotide) [555 nm], and porphyrin [at 585 nm] are higher than due to amino acid tryptophan at (360 nm). That is, in blood plasma, the metabolites due to Hb degradation are elevated twice.

It is important to mention that such dramatic changes in the above ratio parameters occur mostly in long-term smokers. For short-term smokers or "novices" in this habit, the changes are only marginal. This means that we could quantify smoking-induced Hb damages stage by stage.

From the measurement of fluorescent metabolites of Hb as measured by synchronous scan spectroscopy, we would conclude that smoking increases Hb metabolites from 30 to 70%, or in other words, the life span of the Hb gets reduced from 70 to 30% below normal because of smoking.

It is to be understood that the present invention is not limited to the embodiments described above, but encompasses any and all embodiments within the scope of the following claims.

We claim:

1. A spectral method for quantifying hemoglobin fragility caused by smoking, comprising the steps of:
    obtaining control blood samples from at least one non-smoking patient and from a patient having a history of long-term smoking;
    separating blood plasma from the blood samples;
    obtaining synchronous excitation spectra (SXS) of the blood plasma samples with a spectrofluorometer at a scan offset of 70 nm;
    comparing the long-term smoking patient's SXS spectrum with the control SXS spectrum;
    diagnosing hemoglobin fragility when the excitation maximum for tryptophan at 290 nm of the long-term smoking patient is 60% of the control sample;
    obtaining synchronous excitation spectra (SXS) of the blood plasma samples with a spectrofluorometer at a scan offset of 10 nm;
    comparing the long-term smoking patient's SXS spectrum with the control SXS spectrum;
    diagnosing hemoglobin fragility when the excitation maxima of NADH, FAD, and porphyrin for the long-term smoking patient are 30% to 70% higher than the maxima for these metabolites in the control sample;
    computing the ratios $R_1=I555/I360$, $R_2=I360/I555$, and $R_3=I585/I360$, wherein I360 is the intensity of the maximum for tryptophan at 360 nm, I450 is the intensity of the maximum for NADH at 450 nm, I555 is the intensity of the maximum for FAD at 555 nm, and I585 is the intensity of the maximum for porphyrin at 585 nm; and
    diagnosing hemoglobin fragility when $R_1=0.5$, $R_2=0.3$ and $R_3=1.5$ for the long-term smoking patient.

\* \* \* \* \*